(12) United States Patent
Stankus et al.

(10) Patent No.: US 8,480,620 B2
(45) Date of Patent: Jul. 9, 2013

(54) COATINGS WITH TUNABLE SOLUBILITY PROFILE FOR DRUG-COATED BALLOON

(75) Inventors: John Stankus, Campbell, CA (US); Mikael Trollsas, San Jose, CA (US); Syed Hossainy, Hayward, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 455 days.

(21) Appl. No.: 12/636,124

(22) Filed: Dec. 11, 2009

(65) Prior Publication Data

US 2011/0144582 A1 Jun. 16, 2011

(51) Int. Cl.
*A61M 37/00* (2006.01)

(52) U.S. Cl.
USPC ............... 604/103.02; 424/423; 424/426

(58) Field of Classification Search
USPC .................................................. 604/103.02
See application file for complete search history.

(56) References Cited

U.S. PATENT DOCUMENTS

| | | | |
|---|---|---|---|
| 3,929,992 A | 12/1975 | Sehgal |
| 3,993,749 A | 11/1976 | Sehgal |
| 4,316,885 A | 2/1982 | Rakhil |
| 4,401,653 A | 8/1983 | Eng |
| 4,580,568 A | 4/1986 | Gianturco |
| 4,650,803 A | 3/1987 | Stella |
| 4,733,665 A | 3/1988 | Palmaz |
| 4,885,171 A | 12/1989 | Surendra |
| 4,897,268 A | 1/1990 | Tice et al. |
| 4,916,193 A | 4/1990 | Tang |
| 4,994,071 A | 2/1991 | MacGregor |
| 5,023,262 A | 6/1991 | Caufield |
| 5,092,877 A | 3/1992 | Pinchuk |
| 5,102,402 A | 4/1992 | Dror |
| 5,108,416 A | 4/1992 | Ryan et al. |
| 5,120,725 A | 6/1992 | Kao |
| 5,120,727 A | 6/1992 | Kao |
| 5,120,842 A | 6/1992 | Failli |
| 5,163,952 A | 11/1992 | Froix |
| 5,177,203 A | 1/1993 | Failli |
| 5,304,121 A | 4/1994 | Sahatjlan |
| 5,355,832 A | 10/1994 | Loh et al. |
| 5,370,614 A | 12/1994 | Amundson |
| 5,447,724 A | 9/1995 | Helmus |
| 5,457,111 A | 10/1995 | Luly |
| 5,464,650 A | 11/1995 | Berg |
| 5,516,781 A | 5/1996 | Morris |
| 5,527,337 A | 6/1996 | Stack |
| 5,563,146 A | 10/1996 | Morris |
| 5,591,195 A | 1/1997 | Taheri et al. |
| 5,591,227 A | 1/1997 | Dinh et al. |
| 5,605,696 A | 2/1997 | Eury |
| 5,624,411 A | 4/1997 | Tuch |
| 5,646,160 A | 7/1997 | Morris |
| 5,649,977 A | 7/1997 | Campbell |
| 5,665,728 A | 9/1997 | Morris |
| 5,705,583 A | 1/1998 | Bowers |
| 5,720,735 A | 2/1998 | Dorros |
| 5,755,771 A | 5/1998 | Penn et al. |
| 5,767,144 A | 6/1998 | Win |
| 5,843,089 A | 12/1998 | Sahatjian et al. |
| 5,843,172 A | 12/1998 | Yan |
| 5,893,840 A | 4/1999 | Hull et al. |
| 6,015,815 A | 1/2000 | Mollison |
| 6,017,324 A | 1/2000 | Tu et al. |
| 6,033,434 A | 3/2000 | Borghi |
| 6,083,257 A | 7/2000 | Taylor |
| 6,090,901 A | 7/2000 | Bowers |
| 6,106,548 A | 8/2000 | Roubin |
| 6,106,889 A | 8/2000 | Beavers et al. |
| 6,129,705 A | 10/2000 | Grantz |
| 6,146,358 A | 11/2000 | Rowe |
| 6,235,786 B1 | 5/2001 | Dai |
| 6,273,913 B1 | 8/2001 | Wright |
| 6,284,305 B1 | 9/2001 | Ding |
| 6,299,604 B1 | 10/2001 | Ragheb et al. |
| 6,306,144 B1 | 10/2001 | Sydney et al. |
| 6,306,166 B1 | 10/2001 | Barry et al. |
| 6,329,386 B1 | 12/2001 | Mollison |
| 6,335,029 B1 | 1/2002 | Kamath et al. |
| 6,358,556 B1 | 3/2002 | Ding |
| 6,364,856 B1 | 4/2002 | Ding et al. |
| 6,368,658 B1 | 4/2002 | Schwarz et al. |
| 6,406,457 B1 | 6/2002 | Wang |

(Continued)

FOREIGN PATENT DOCUMENTS

| | | |
|---|---|---|
| DE | 102007034991 | 1/2009 |
| EP | 0467606 A1 | 1/1992 |
| EP | 0184162 B1 | 4/1994 |
| EP | 0623354 | 11/1994 |
| WO | WO 92/05179 | 4/1992 |
| WO | WO 01/87372 | 11/2001 |
| WO | WO 02/055122 | 7/2002 |
| WO | WO 03/022324 | 3/2003 |
| WO | WO 2004/022124 | 3/2004 |
| WO | WO 2004/037443 | 5/2004 |

(Continued)

OTHER PUBLICATIONS

U.S. Appl. No. 12/636,158, Oct. 12, 2011 Non-Final Office Action.
U.S. Appl. No. 12/371,426, Aug. 5, 2011 Non-Final Office Action.
U.S. Appl. No. 12/371,422, Aug. 5, 2011 Non-Final Office Action.
U.S. Appl. No. 11/084,172, Sep. 23, 2011 Issue Fee Paid.
U.S. Appl. No. 11/084,172, Sep. 19, 2011 Notice of Allowance.

(Continued)

*Primary Examiner* — Frederick Krass
*Assistant Examiner* — Adam C Milligan
(74) *Attorney, Agent, or Firm* — Baker Botts L.L.P.

(57) ABSTRACT

A drug delivery balloon is provided, the a balloon having an outer surface, and a tunable coating disposed on at least a length of the balloon surface. The tunable coating includes a first therapeutic agent and a first excipient, and a second therapeutic agent and a second excipient. The first and second therapeutic agents have different dissolution rates during balloon inflation and therefore provide a coating that is tunable.

10 Claims, 3 Drawing Sheets

U.S. PATENT DOCUMENTS

| | | |
|---|---|---|
| 6,413,272 B1 | 7/2002 | Igak |
| 6,419,692 B1 | 7/2002 | Yang |
| 6,500,148 B1 | 12/2002 | Pinchuk |
| 6,521,658 B1 | 2/2003 | Li |
| 6,585,764 B2 | 7/2003 | Wright |
| 6,616,650 B1 | 9/2003 | Rowe |
| 6,669,980 B2 | 12/2003 | Hansen |
| 6,682,553 B1 | 1/2004 | Webler, Jr. |
| 6,682,556 B1 | 1/2004 | Ischinger |
| 6,709,440 B2 | 3/2004 | Matin et al. |
| 6,726,923 B2 | 4/2004 | Iyer et al. |
| 6,991,617 B2 | 1/2006 | Hektner |
| 7,048,714 B2 | 5/2006 | Richter |
| 7,087,263 B2 | 8/2006 | Hossainy et al. |
| 7,241,344 B2 | 7/2007 | Worsham |
| 7,273,417 B1 | 9/2007 | Lundquist |
| 7,357,942 B2 | 4/2008 | Burke et al. |
| 7,378,105 B2 | 5/2008 | Burke et al. |
| 7,396,539 B1 | 7/2008 | Hossainy et al. |
| 7,399,480 B2 | 7/2008 | Mollison et al. |
| 7,445,792 B2 | 11/2008 | Toner et al. |
| 7,455,853 B2 | 11/2008 | Mollison et al. |
| 7,572,245 B2 | 8/2009 | Herweck et al. |
| 2002/0123505 A1 | 9/2002 | Mollison et al. |
| 2002/0183581 A1 | 12/2002 | Yoe et al. |
| 2002/0193828 A1* | 12/2002 | Griffin et al. ............ 606/200 |
| 2003/0129215 A1 | 7/2003 | Mollison |
| 2003/0170287 A1 | 9/2003 | Prescott |
| 2003/0204238 A1 | 10/2003 | Tedeschi |
| 2003/0216699 A1 | 11/2003 | Falotico |
| 2004/0073284 A1 | 4/2004 | Bates et al. |
| 2004/0224003 A1* | 11/2004 | Schultz ................ 424/423 |
| 2004/0225345 A1 | 11/2004 | Fischell et al. |
| 2004/0234748 A1 | 11/2004 | Stenzel |
| 2004/0254635 A1 | 12/2004 | Shanley et al. |
| 2004/0267352 A1 | 12/2004 | Davidson et al. |
| 2005/0004661 A1 | 1/2005 | Lewis |
| 2005/0019404 A1 | 1/2005 | Sung et al. |
| 2005/0036946 A1 | 2/2005 | Pathak et al. |
| 2005/0106206 A1 | 5/2005 | Herweck et al. |
| 2005/0149173 A1 | 7/2005 | Hunter et al. |
| 2005/0163818 A1 | 7/2005 | Sung et al. |
| 2005/0163913 A1 | 7/2005 | Spencer et al. |
| 2005/0169957 A1 | 8/2005 | Hossainy |
| 2005/0178396 A1* | 8/2005 | Hunter et al. ............ 128/898 |
| 2005/0246009 A1 | 11/2005 | Toner et al. |
| 2005/0250672 A9 | 11/2005 | Speck et al. |
| 2006/0020243 A1 | 1/2006 | Speck et al. |
| 2006/0171984 A1 | 8/2006 | Cromack et al. |
| 2006/0198867 A1 | 9/2006 | Toner et al. |
| 2007/0027523 A1 | 2/2007 | Toner et al. |
| 2007/0088255 A1 | 4/2007 | Toner et al. |
| 2007/0224240 A1 | 9/2007 | Toner et al. |
| 2008/0003254 A1 | 1/2008 | Mack et al. |
| 2008/0057101 A1 | 3/2008 | Roorda |
| 2008/0255508 A1 | 10/2008 | Wang |
| 2008/0262589 A1 | 10/2008 | Nagura |
| 2008/0300675 A1* | 12/2008 | Penhasi ................ 623/1.49 |
| 2009/0162413 A1 | 6/2009 | Toner et al. |
| 2009/0285974 A1 | 11/2009 | Kerrigan |
| 2010/0023108 A1 | 1/2010 | Toner et al. |
| 2010/0030183 A1 | 2/2010 | Toner et al. |
| 2010/0076377 A1 | 3/2010 | Ehrenreich |
| 2010/0076401 A1 | 3/2010 | Von Oepen |

FOREIGN PATENT DOCUMENTS

| | | |
|---|---|---|
| WO | WO 2005/089855 | 9/2005 |
| WO | WO 2006/024492 | 3/2006 |
| WO | WO 2006/116348 | 11/2006 |
| WO | WO 2007/032777 | 3/2007 |
| WO | WO 2007/046935 | 4/2007 |
| WO | WO 2007/065722 | 6/2007 |
| WO | WO 2007/109372 | 9/2007 |
| WO | WO 2008/021124 | 2/2008 |
| WO | WO 2008/089730 | 7/2008 |
| WO | WO 2009/051614 | 4/2009 |
| WO | WO 2010/027735 | 3/2010 |
| WO | WO 2010/030995 | 3/2010 |
| WO | WO 2010/093799 | 8/2010 |

OTHER PUBLICATIONS

U.S. Appl. No. 11/548,827, Aug. 3, 2011 Request for Continued Examination (RCE).
U.S. Appl. No. 11/548,827, May 3, 2011 Final Office Action.
U.S. Appl. No. 12/090,253, Sep. 26, 2011 Response to Restriction Requirement.
U.S. Appl. No. 12/090,253, Aug. 24, 2011 Restriction Requirement.
Reil et al., Journal of Surgical Research, 1999, 85: 109-114.
Roberge et al., Ocular Immunology and Inflammation, 1995, 3: 195-202.
U.S. Appl. No. 12/371,422, Jan. 20, 2012 Final Office Action.
U.S. Appl. No. 12/371,422, Jan. 6, 2012 Applicant Summary of Interview with Examiner.
U.S. Appl. No. 12/371,422, Dec. 30, 2011 Applicant Initiated Interview Summary.
U.S. Appl. No. 12/371,422, Dec. 22, 2011 Supplemental Response to Office Action.
U.S. Appl. No. 12/371,422, Nov. 7, 2011 Response to Office Action.
U.S. Appl. No. 12/371,426, Feb. 1, 2012 Final Office Action.
U.S. Appl. No. 12/371,426, Jan. 5, 2012 Applicant Initiated Interview Summary.
U.S. Appl. No. 12/371,426, Nov. 7, 2011 Response to Non-Final Office Action.
U.S. Appl. No. 11/483,030, Feb. 2, 2012 Non-Final Office Action.
U.S. Appl. No. 12/090,253, Dec. 8, 2011 Non-Final Office Action.
U.S. Appl. No. 11/539,944, Feb. 6, 2012 Non-Final Office Action.
U.S. Appl. No. 12/371,422, Apr. 20, 2012 Amendment and Request for Continued Examination (RCE).
U.S. Appl. No. 12/371,426, May 1, 2012 Amendment and Request for Continued Examination (RCE).
U.S. Appl. No. 11/483,030, May 2, 2012 Response to Non-Final Office Action.
U.S. Appl. No. 11/539,944, May 7, 2012 Response to Non-Final Office Action.
U.S. Appl. No. 12/636,158, Mar. 12, 2012 Response to Non-Final Office Action.
U.S. Appl. No. 12/371,426, Apr. 2, 2012 Response to Final Office Action.
U.S. Appl. No. 12/636,158, May 23, 2012 Final Office Action.
U.S. Appl. No. 12/636,079, Aug. 27, 2012 Response to Examiner's Interview Summary.
U.S. Appl. No. 12/636,079, Jul. 26, 2012 Applicant-Initiated Interview Summary.
U.S. Appl. No. 12/371,426, Aug. 27, 2012 Supplemental Amendment and Statement of the Substance of the Interview.
U.S. Appl. No. 12/371,426, Aug. 2, 2012 Applicant-Initiated Interview Summary.
U.S. Appl. No. 12/371,422, Aug. 27, 2012 Filed Supplemental Amendment, Statement of the Subastance of the Interview and Supplemental Declaration.
U.S. Appl. No. 12/371,422, Jul. 25, 2012 Applicant-Initiated Interview Summary.
U.S. Appl. No. 12/636,158, Aug. 30, 2012 Applicant-Initiated Interview Summary.
U.S. Appl. No. 12/636,158, Aug. 20, 2012 Applicant-Initiated Interview Summary.
U.S. Appl. No. 12/090,253, Jun. 1, 2012 Final Office Action.
U.S. Appl. No. 12/090,253, Apr. 9, 2012 Response to Non-Final Office Action.
U.S. Appl. No. 11/483,030, Jul. 19, 2012 Final Office Action.
U.S. Appl. No. 11/539,944, Aug. 3, 2012 Final Office Action.
Heldman, et al., "Paclitaxel stent coating inhibits neointimal hyperplasia at 4 weeks in a porcine model of coronary restenosis", *Circulation*, 103(18):2289-95 (2001).
U.S. Appl. No. 13/617,628, filed Sep. 14, 2012.
U.S. Appl. No. 12/636,158, Oct. 23, 2012 Amendment and Request for Continued Examination (RCE).
U.S. Appl. No. 13/617,628, Nov. 30, 2012 Non-Final Office Action.

U.S. Appl. No. 11/548,827, Dec. 24, 2012 Examiner Initiated Interview Summary.
U.S. Appl. No. 11/548,827, Nov. 9, 2012 Notice of Allowance.
U.S. Appl. No. 12/371,422, Dec. 20, 2012 Notice of Allowance.
U.S. Appl. No. 12/090,253, Dec. 28, 2012 Notice of Abandonment.
The International Search Report and Written Opinion from PCT/US2010/023907, filed Jun. 21, 2010, Abbott Laboratories.
U.S. Appl. No. 12/636,158, filed Dec. 11, 2009.
U.S. Appl. No. 12/636,079, filed Dec. 11, 2009.
U.S. Appl. No. 11/539,944, Non-final Office Action issued on Mar. 16, 2009.
U.S. Appl. No. 11/539,944, Response to the Non-final Office Action filed on Jun. 29, 2009.
U.S. Appl. No. 11/539,944, Final Office Action issued on Sep. 2, 2009.
U.S. Appl. No. 11/539,944, Feb. 2, 2010 Response to Final Office Action.
U.S. Appl. No. 11/539,944, Apr. 26, 2010 Preliminary amendment.
U.S. Appl. No. 11/539,944, May 12, 2010 Non-Final Office Action.
U.S. Appl. No. 11/539,944, Aug. 12, 2010 Response to Non-Final Office Action.
U.S. Appl. No. 11/548,827, May 29, 2009 Non-Final Office Action.
U.S. Appl. No. 11/548,827, Aug. 14, 2009 Response to Non-Final Office Action.
U.S. Appl. No. 11/548,827, Oct. 12, 2009 Response to Non-Final Office Action.
U.S. Appl. No. 11/548,827, Jan. 25, 2010 Final Office Action.
U.S. Appl. No. 11/548,827, Mar. 25, 2010 Response to Final Office Action.
U.S. Appl. No. 11/548,827, Apr. 21, 2010 Advisory Action.
U.S. Appl. No. 11/548,827, Apr. 28, 2010 Request for Continued Examination (RCE).
U.S. Appl. No. 11/084,172, Apr. 22, 2010 Response to Final Office Action and RCE.
U.S. Appl. No. 11/483,030, Non-final Office Action issued on Mar. 31, 2009.
U.S. Appl. No. 11/483,030, Response to the Non-final Office Action filed on Jun. 29, 2009.
U.S. Appl. No. 11/483,030, Final Office Action issued on Sep. 2, 2009.
U.S. Appl. No. 11/483,030, Feb. 2, 2010 Response to Final Office Action.
U.S. Appl. No. 11/483,030, Apr. 26, 2010 Preliminary Amendment and Applicant summary of interview with examiner.
U.S. Appl. No. 11/483,030, May 12, 2010 Non-Final Rejection.
U.S. Appl. No. 11/483,030, Aug. 12, 2010 Response to Non-Final Office Action.
U.S. Appl. No. 11/084,172, Restriction Requirement issued on Sep. 20, 2007.
U.S. Appl. No. 11/084,172, Response to the Restriction Requirement filed Oct. 22, 2007.
U.S. Appl. No. 11/084,172, Non-Final Office Action issued on Jan. 9, 2008.
U.S. Appl. No. 11/084,172, Response to the Non-Final Office Action filed Apr. 7, 2008.
U.S. Appl. No. 11/084,172, Final Office Action issued on Jul. 3, 2008.
U.S. Appl. No. 11/084,172, Response to the Final Office Action filed Sep. 3, 2008.
U.S. Appl. No. 11/084,172, RCE filed Dec. 31, 2008.
U.S. Appl. No. 11/084,172, Response to the Final Office Action filed Jan. 22, 2009.
U.S. Appl. No. 11/084,172, Non-final Office Action issued on Apr. 29, 2009.
U.S. Appl. No. 11/084,172, Response to the Non-Final Office Action filed Sep. 29, 2009.
U.S. Appl. No. 11/084,172, Jan. 22, 2010 Final Office Action.
The PCT Search Report for PCT/US2005/009310, filed Mar. 17, 2005, mailed Jul. 25, 2005.
Boland et al. *International Journal of Cardiovascular Interventions*, 2000, 3:215-225.
Wei et al. *Journal of Cardiothoracic and Vascular Anesthesia*, 2001, 4:455-459.
Salem et al. *International Archives of Allergy and Immunology*, 2000 121:235-245.
Stella, "A Case for Prodrugs in Prodrugs: Challenges and Rewards Part I," Eds. Stella et al. New York: Springer, 2007. 1-33.
International Search Report for PCT/US2006/040027, 2006.
International Search Report for PCT/US2007/021846, 2007.
Supplementary European Search Report for Appl. No. EP06825887, 2006.
Aggarwal, A., D.J. Schneider, B.E. Sobel, and H.L. Dauerman. 2003. "Comparison of inflammatory markers in patients with diabetes mellitus versus those without before and after coronary arterial stenting." *Am J Cardiol*. 92:924-9.
Baker, H., A. Sldorowicz, S.N. Sehgal, and C. Vezina. 1978. "Raparnycin (AY-22,989), a new antifungal antibiotic. III. In vitro and in vivo evaluation." *J Antibiot* (Tokyo). 31:539-45.
Bierer, B.E., S.L. Schreiber, and S.J. Burakoff. 1991. "The effect of the immunosuppressant FK-506 on alternate pathways of T cell activation." *Eur J lmrnuno*. 21:439-45.
Biondi-Zoccai, G.G., A. Abbate, G. Liuzzo, and L.M. Biasucci. 2003. "Atherothrombosis, lnflarnmation, and diabetes.". *J Am Coll Cardiol*. 41:1071-7.
Brown, E.J., M.W. Albers, T.B. Shin, K. Ichikawa, C.T. Keith, W.S. Lane, and S.L. Schreiber. 1994. "A mammalian protein targeted by GI-arresting rapamycin-receptor complex." *Nature*. 369:756-8.
Bunchman, T.E., and C.A. Brookshire. 1991. "Smooth muscle cell proliferation by conditioned media from cyclosporinetreated endothelial cells: a role of endothelin." *Transplant Proc*. 23:967-8.
Carter, A.J., M. Aggarwal, G.A. Kopia, F. Tio, P.S. Tsao, R. Kolata, A.C. Yeung, G. Llanos, J. Dooley, and R. Falotico.2004. "Long-term effects of polymer-based, slow-release, sirolimus-eluting stents in a porcine coronary model." *Cardiovasc Res*. 63:617-24.
Dandona, P., and A. Aljada. 2002. "A rational approach to pathogenesis and treatment of type 2 diabetes mellitus, insulin resistance, inflammation, and atherosclerosis." *Am J Cardiol*. 90:27G-33G.
Dumont, F.J., M.R. Melino, M.J. Staruch, S.L. Koprak, P.A. Fischer, and N.H. Sigal. 1990. The immunosuppressive macrolides FK-506 and rapamycin act as reciprocal antagonists in murine T cells. J Immunol. 144:1418-24.
Fretz, H., M. Albers, A. Gala, R. Standaert, W. Lane, S. Burakoff, B. Bierer, and S. Schreiber. 1991. "Rapamycin and FK506 binding proteins (immunophilins)." *J. Am. Chem. Soc*. 113:1409-1411.
Grech, E.D., and D.R. Ramsdale. 2003. "Acute coronary syndrome: unstable angina and non-ST segment elevation myocardial infarction." *British Med*. J. 326:1259-61.
Harding, M.W., A. Galat, D.E. Uehling, and S.L. Schreiber. 1989. "A receptor for the immunosuppressant FK506 is a cis-trans peptidyl-proyl isomerase." *Nature*. 341:758-60.
Hayward, C., D. Yohannes, and S. Danishefsky. 1993. "Total synthesis of rapamycin via a novel titanium-mediated aldol macrocyclization reaction." J. *Am.Chem. Soc*. 11 5:9345-9346.
Helmus, M. 1990. "Medical Device Design—A Systems Approach: Central Venous Catheters." In 22nd International Society for the Advancement of Material and Process Engineering Technical Conference.
Ji, Q., M. Reimer, and T. El-Shourbagy. 2004."96-well liquid-liquid extraction liquid chromatography-tandem mass spectrometry method for the quantitative determination of ABT-578 in human blood samples." *Journal of Chromatography* B. 805:67-75.
Kino, T., N. Inamura, F. Sakai, K. Nakahara, T. Goto, M. Okuhara, M. Kohsaka, H. Aoki, and T. Ochiai. 1987. "Effect of FK-506 on human mixed lymphocyte reaction in vitro." *Transplant Proc*. 19:36-9.
Kornowski, R., M.K. Hong, F.O. Tio, 0. Bramwell, H. Wu, and M.B. Leon. 1998. "In-stent restenosis: contributions of inflammatory responses and arterial injury to neointimal hyperplasia." *J Am Coll Cardiol*. 31:224-30.
Martel, R.R., J. Klicius, and S. Galet. 1977. "Inhibition of the immune response by rapamycin, a new antifungal antibiotic." *Can J Physiol Pharmacol*. 55:48-51.
Morris, R. 1992. "Rapamycins: antifungal, antitumor, antiproliferative, and immunosuppressive macrolides." *Transplant. Rev*. 6:39-87.
Morris, R., and B. Meiser. 1989. "Identification of a new pharmacologic action for an old compound." *Med Sci. Res*. 17:609-610.

Nicolaou, K., T. Chakraborty, A. Piscopio, N. Minowa, and P. Bertinato. 1993. "Total synthesis of rapamycin." *J. Am. Chem. Soc.* 115:4419-4420.

Paiva, N.L., A.L. Demain, and M.F. Roberts. 1991. "Incorporation of acetate, propionate, and methionine into rapamycin by *Streptomyces hygroscopicus.*" *J Nat Prod* 54:167-77.

Roffi, M., and E.J. Topol. 2004. "Percutaneous coronary intervention in diabetic patients with non-ST-segment elevation acute coronary syndromes." *Eur Heart J.* 25:190-8.

Romo, D., S. Meyer, D. Johsnon, and S. Schrieber. 1993. "Total synthesis of (−)-rapamycin using an Evans-Tishchenko fragment coupling." *J. Am. Chem. Soc.* 115:7906-7907.

Sabatini, D.M., H. Erdjument-Bromage, M. Lui, P. Tempst, and S.H. Snyder. 1994. "RAFTI: a mammalian protein that binds to FKBPIZ in a rapamycin-dependent fashion and is homologous to yeast TORS." *Cell.* 78:35-43.

Schwartz, R. et al., 1992. "Restenosis and the proportional neointimal response to coronary artery injury: results in a porcine model." *J Am Coll Cardiol.* 19:267-274.

Sehgal, S.N., H. Baker, C.P. Eng, K. Singh, and C. Vezina. 1983. "Demethoxyrapamycin (AY-24,668), a new antifungal antibiotic." *J Antibiot* (Tokyo). 36:351-4.

Sehgal, S.N., H. Baker, and C. Vezina. 1975. "Rapamycin (AY-22,989), a new antifungal antibiotic. II. Fermentation, isolation and characterization." *J Antibiot* (Tokyo). 28:727-32.

Shichiri, M., Y. Hirata, T. Nakajima, K. Ando, T. Imai, M. Yanagisawa, T. Masaki, and F. Marumo. 1991. "Endothelin-I is an autocrine/paracrine growth factor for human cancer cell lines." *J Clin Invest.* 87:1867-71.

Siekierka, J.J., S.H. Hung, M. Poe, C.S. Lin, and N.H. Sigal. 1989. "A cytosolic binding protein for the immunosuppressant FK506 has peptidyl-prolyl isomerase activity but is distinct from cyclophilin." *Nature.* 341:755-7.

Suzuki, T., G. Kopia, S. Hayashi, L.R. Bailey, G. Llanos, R. Wilensky, B.D. Klugherz, G. Papandreou, P. Narayan, M.B. Leon, A.C. Yeung, F. Tio, P.S. Tsao, R. Falotico, and A.J. Carter. 2001. "Stent-based delivery of sirolimus reduces neointimal formation in a porcine coronary model." *Circulation.* 104:1188-93.

Vezina, C., A. Kudelski, and S.N. Sehgal. 1975. "Rapamycin (AY-22,989), a new antifungal antibiotic. I. Taxonomy of the producing streptomycete and isolation of the active principle." *J Antibiot* (Tokyo). 28:721-6.

Yamagishi, S., C.C. Hsu, K. Kobayashi, and H. Yamamoto. 1993. "Endothelin 1 mediates endothelial cell-dependent proliferation of vascular pericytes." *Biochem Biophys Res Commun.* 191:840-6.

Yudkin, J.S., M. Kumari, S.E. Humphries, and V. Mohamed-Ali. 2000. "Inflammation, obesity, stress and coronary heart disease: is interleukin-6 the LINK?" *Atherosclerosis.* 148:209-14.

Levin et al., "Specific binding to intracellular proteins determines arterial transport properties for rapamycin and paclitaxel." *PNAS* vol. 101, No. 25, pp. 9463-9467 (2004).

Van der Hoeven et al., "Drug-eluting stents: results, promises and problems," *Int. J. of Cardiology* 99, pp. 9-17 (2005).

Unverdorben et al., 2009, "Paclitaxel-coated balloon catheter versus paclitaxel-coated stent for the treatment of coronary in-stent restenosis." *Circulation* 119:2986-2994.

Stiles, "Paclitaxel-coated balloon cuts late lumen loss after PCI for in-stent restenosis," The Heart.org from *WebMD*, Apr. 4, 2008. Downloaded from <http://www.theheart.org/article/855221/print.do> on Sep. 28, 2009.

B. Braun Melsungen A.G. Press release, "Drug-coated balloon overcomes in-stent restenosis," Apr. 2, 2008. B. Braun Melsungen A.G. website. Downloaded from <http://www.bbraun.com/cps/rde/xchg/bbraun-com/hs.xsl/news_drug-coated-balloon-overcomes-in-stent-restenosis.html?from=newssearch> on Sep. 28, 2010.

U.S. Appl. No. 11/539,944, Mar. 16, 2009 Non-final Office Action.
U.S. Appl. No. 11/539,944, Jun. 29, 2009 Response to the Non-final Office Action.
U.S. Appl. No. 11/539,944, Sep. 2, 2009 Final Office Action.
U.S. Appl. No. 11/548,827, Oct. 1, 2010 Non-Final Office Action.
U.S. Appl. No. 11/548,827, Mar. 1, 2011 Response to Non-Final Office Action.
U.S. Appl. No. 11/483,030, Mar. 31, 2009 Non-final Office Action.
U.S. Appl. No. 11/483,030, Jun. 29, 2009, Response to the Non-final Office Action.
U.S. Appl. No. 11/483,030, Sep. 2, 2009 Final Office Action.
U.S. Appl. No. 11/483,030 Apr. 26, 2010, Preliminary Amendment and Applicant summary of interview with examiner.
U.S. Appl. No. 11/483,030, Oct. 29, 2010 Final Office Action.
U.S. Appl. No. 11/483,030, Jan. 31, 2011 Request for Continued Examination (RCE).
U.S. Appl. No. 11/084,172, Sep. 20, 2007 Restriction Requirement.
U.S. Appl. No. 11/084,172, Oct. 22, 2007 Response to the Restriction Requirement.
U.S. Appl. No. 11/084,172, Jan. 9, 2008 Non-Final Office Action.
U.S. Appl. No. 11/084,172, Apr. 7, 2008 Response to the Non-Final Office Action.
U.S. Appl. No. 11/084,172, Jul. 3, 2008 Final Office Action.
U.S. Appl. No. 11/084,172, Sep. 3, 2008 Response to the Final Office Action.
U.S. Appl. No. 11/084,172, Dec. 31, 2008 Request for Continued Examination (RCE).
U.S. Appl. No. 11/084,172, Jan. 22, 2009 Response to the Final Office Action.
U.S. Appl. No. 11/084,172, Apr. 29, 2009 Non-final Office Action.
U.S. Appl. No. 11/084,172, Sep. 29, 2009 Response to the Non-Final Office Action.
International Search Report for PCT/US2005/009310, 2005.
International Search Report and Written Opinion for PCT/US2010/055806, 2011.
Partial International Search Report for PCT/US2010/055809, 2011.
International Search Report and Written Opinion for PCT/US2010/055818, 2011.
International Search Report and Written Opinion for PCT/US2010/023907, 2011.
European Search Report issued on Mar. 1, 2011 in application No. EP10011851.2 (corresponding to US 2010/0030183A1).
Baker, H., A. Sldorowicz, S.N. Sehgal, and C. Vezina. 1978. "Rapamycin (AY-22,989), a new antifungal antibiotic. III. In vitro and in vivo evaluation." *J Antibiot* (Tokyo). 31 :539-45.
Biondi-Zoccai, G.G., A. Abbate, G. Liuzzo, and L.M. Biasucci. 2003. "Atherothrombosis, Inflammation, and diabetes.". *J Am Coll Cardiol.* 41 :1071-7.
Cremers, et al., "Inhibition of Coronary Neointimal Hyperplasia in Swine Using a Novel Zotarolimus-Eluting Balloon Catheter", *European Society of Cardiology*, XP002616155, Aug. 31, 2009, URL:HTTP://spo.escardio.org/eslides/view.aspx?eevtid=33&fp=3206.
Hayward, C., D. Yohannes, and S. Danishefsky. 1993. "Total synthesis of rapamycin via a novel titanium-mediated aldol macrocyclization reaction." *J. Am. Chem. Soc.* 11 5:9345-9346.
Morris, R., and B. Meiser. 1989. "Identification of a new pharmacologic action for an old compound." *Med. Sci. Res.* 17:609-610.
Nicolaou, K., T. Chakraborty, A. Piscopio, N. Minowa, and P. Bertinato. 1993. "Total synthesis of rapamycin." *J Am. Chem. Soc.* 115:4419-4420.
Paiva, N.L., A.L. Demain, and M.F. Roberts. 1991. "Incorporation of acetate, propionate, and methionine into rapamycin by *Streptomyces hygroscopicus.*" *J Nat Prod.* 54:167-77.
Richard, et al., "Controlled Delivery of Paclitaxel from stent Coatings Using Novel Styrene Maleic Anhydride Copolymer Formulations", *Journal of Biomedical Materials Research*, vol. 90A, No. 2, pp. 522-523, Jun. 18, 2008, www.interscience.wiley.com.
Roffi, M., and E.J. Topol. 2004. "Percutaneous coronary intervention in diabetic patients with non-ST-segment elevation acute coronary syndromes." *Eur Heart J* 25:190-8.
Roma, D., S. Meyer, D. Johsnon, and S. Schrieber. 1993. "Total synthesis of (−)-rapamycin using an Evans-Tishchenko fragment coupling." *J. Am. Chem. Soc.* 115:7906-7907.
Siekierka, J.J., S.H. Hung, M. Poe, C.S. Lin, and N.H. Sigal. 1989. "A cytosolic binding protein for the immunosuppressant FK506 has peptidyl-prolyl isomerase activity but is distinct from cyclophilin." *Nature.* 341 :755-7.

Suzuki, T., G. Kopia, S. Hayashi, L.R. Bailey, G. Llanos, R. Wilensky, B.D. Klugherz, G. Papandreou, P. Narayan, M.B. Leon, A.C. Yeung, F. Tia, P.S. Tsao, R. Falotico, and A.J. Carter. 2001. "Stent-based delivery of sirolimus reduces neointimal formation in a porcine coronary model." *Circulation*. 104:1188-93.

Van der Hoeven et al., "Drug-eluting stents: results, promises and problems," *Int. J of Cardiology* 99, pp. 9-17 (2005).

Burke et al., "Zotarolimus (ABT-578) eluting stents", *Advanced Drug Delivery Reviews*, Mar. 6, 2006, 58: 437-446.

International Search Report and Written Opinion for PCT/US2010/023910, 2010.

U.S. Appl. No. 13/617,628, Apr. 3, 2013 Notice of Allowance.

U.S. Appl. No. 13/617,628, Feb. 28, 2013 Response to Non-Final Office Action.

U.S. Appl. No. 12/371,422, Mar. 20, 2013 Issue Fee payment.

U.S. Appl. No. 12/636,079, Apr. 18, 2013 Non-Final Office Action.

\* cited by examiner

COATINGS WITH TUNABLE SOLUBILITY PROFILE FOR DRUG-COATED BALLOON

FIELD OF THE INVENTION

The disclosed subject matter is related to the delivery of drugs from an insertable medical device. More particularly, the disclosed subject matter relates to a medical device including a balloon for delivery of a therapeutic agent, the balloon having a tunable coating disposed on its outer surface.

BACKGROUND OF THE INVENTION

Atherosclerosis is a syndrome affecting arterial blood vessels. It is a chronic inflammatory response in the walls of arteries, which is in large part due to the accumulation of lipid, macrophages, foam cells and the formation of plaque in the arterial wall. Atherosclerosis is commonly referred to as hardening of the arteries although the pathophysiology of the disease manifests itself with several different types of lesions ranging from fibrotic to lipid laden to calcific. Angioplasty is a vascular interventional technique involving mechanically widening an obstructed blood vessel, typically caused by atherosclerosis.

During angioplasty, a catheter having a tightly folded balloon is inserted into the vasculature of the patient and is passed to the narrowed location of the blood vessel at which point the balloon is inflated to a desired size and pressure using an inflation fluid, typically angiographic contrast media. Percutaneous coronary intervention (PCI), commonly known as coronary angioplasty, is a therapeutic procedure to treat the stenotic coronary arteries of the heart, often found in coronary heart disease.

In contrast, peripheral angioplasty, commonly known as percutaneous transluminal angioplasty (PTA), refers to the use of mechanical widening of blood vessels other than the coronary arteries. PTA is most commonly used to treat narrowing of the leg arteries, especially, the iliac, external iliac, superficial femoral and popliteal arteries. PTA can also treat narrowing of veins, and other blood vessels.

Although the blood vessel is often successfully widened by angioplasty, sometimes the treated wall of the blood vessel experienced abrupt closure after balloon inflation or dilatation due to acute recoil or vasospasm. Interventional cardiologists addressed this problem by stenting the blood vessel to prevent acute recoil and vasospasm. A stent is a device, typically a metal tube or scaffold, that was inserted into the blood vessel following angioplasty, in order to hold the blood vessel open.

While the advent of stents eliminated many of the complications of abrupt vessel closure after angioplasty procedures, within about six months of stenting, a re-narrowing of the blood vessel can form, a condition known as restenosis. Restenosis was discovered to be a response to the injury of the angioplasty procedure and is characterized by a growth of smooth muscle cells—analogous to a scar forming over an injury. As a solution, drug eluting stents were developed to address the reoccurrence of the narrowing of blood vessels. One example of a drug eluting stent is a metal stent that has been coated with a drug that is known to interfere with the process of restenosis. A potential drawback of certain drug eluting stents is known as late stent thrombosis, which is an event in which blood clots inside the stent.

Drug eluting balloons are believed to be a viable alternative to drug eluting stents in the treatment of atherosclerosis. In a study which evaluated restenosis and the rate of major adverse cardiac events such as heart attack, bypass, repeat stenosis, or death in patients treated with drug eluting balloons and drug eluting stents, the patients treated with drug eluting balloons experienced only 3.7 percent restenosis and 4.8% MACE (major adverse coronary events) as compared to patients treated with drug eluting stents, in which restenosis was 20.8 percent and 22.0 percent MACE rate. (See, PEPCAD II study, Rotenburg, Germany).

Although drug eluting balloons are a viable alternative, and in some cases appear to have greater efficacy than drug eluting stents as suggested by the PEPCAD II study, drug eluting balloons present challenges due to the very short period of contact between the drug coated balloon surface and the blood vessel wall. In particular, the balloon can only be inflated for less than one minute, and is often inflated for only thirty seconds. Therefore, an efficacious, therapeutic amount of drug must be transferred to the vessel wall within a thirty second to one minute time period. For the peripheral vasculature, the allowable inflation times can be greater than one minute, but are still measured in minutes. Thus, there are challenges specific to drug delivery via a drug coated balloon because of the necessity of a short inflation time, and therefore time for drug or coating transfer—a challenge not presented by a drug eluting stent, which remains in the patient's vasculature once implanted.

Other considerations are the current theories about the mechanism by which a drug coated balloon transfers drug to the vessel wall. One theory, for example, is that upon balloon expansion, drug mechanically fractures or dissolves from the coating, diffuses to the vessel wall and then permeates into the vessel wall. A second theory is that upon balloon expansion the balloon coating is transferred to the vessel wall and then drug permeates into the vessel wall from the coating adhered to the vessel wall. Another theory is that the balloon expansion creates tears and microfissures in the vessel wall and a portion of the coating inserts into the tears and microfissures. Drug then permeates into the vessel wall from the coating within the tears and fissures. Yet another theory is that upon balloon expansion, a layer of dissolved drug and coating excipients is formed at a high concentration on the vessel wall as a boundary layer. The drug diffuses and permeates from this boundary layer into the vessel wall. In most of these theories, the drug transfers from the balloon to the circulation or the vascular wall tissue upon fracture of the coating due to inflation of the balloon and occurs within one minute, and preferably within 30 seconds. Therefore, a need exists for a drug coated balloon having efficient drug transfer to a vessel wall.

Various embodiments of drug-coated balloons have been proposed, including balloons with a therapeutic agent disposed directly on the balloon surface and balloons having various protective sheaths. However, not all embodiments result in an efficacious response in reducing restenosis after balloon and bare metal stent trauma.

Therefore, a need exists for a drug eluting balloon and more particularly, a balloon coated with a therapeutic agent that provides for effective delivery kinetics of the therapeutic agent from the surface of the balloon.

SUMMARY OF INVENTION

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

In accordance with one embodiment of the disclosed subject matter, a drug delivery balloon is provided for delivering at least one therapeutic agent to a vasculature or tissue. The balloon catheter has an elongate tubular member having a proximal end, a distal end and a lumen therebetween. An expandable balloon is attached to the distal end of the elongate tubular member. The balloon has an outer surface having a tunable coating disposed on at least a length of the outer surface, the tunable coating including a first therapeutic agent and a first excipient, and a second therapeutic agent and a second excipient. In accordance with the present subject matter, the first and second therapeutic agents have different dissolution rates during balloon inflation. The different dissolution rates define the tunable solubility. The coating has a biosolubility that is tunable based on the therapeutic agents and excipients that are selected.

In accordance with one embodiment, the first therapeutic agent is different than the second therapeutic agent. In accordance with the disclosed subject matter, the solubility of the coating can be modified depending on the molecular weight of the excipient. In accordance with one embodiment, the excipient is a polymer having a molecular weight of less than about 35 kDalton. In accordance with yet another embodiment, the excipient is a polymer having a molecular weight greater than about 100 kDalton. In accordance with another embodiment, the coating includes a third therapeutic agent and a third excipient.

In accordance with the disclosed subject matter, the solubility of the coating can be tuned by selecting a certain type of excipient. In accordance with a preferred embodiment of the disclosed subject matter, the excipient includes polyvinylpyrrolidone, silk-elastin like protein polymers, biodegradable polymers, and polyvinylidene fluoride, carboxylated aromatic compound. In accordance with one embodiment, the first excipient is the same as the second excipient. Alternatively, the first excipient is different from the second excipient.

The therapeutic agent can include anti-proliferative, anti-inflammatory, antineoplastic, antiplatelet, anti-coagulant, anti-fibrin, antithrombotic, antimitotic, antibiotic, antiallergic and antioxidant compounds. In accordance with a preferred embodiment, the therapeutic agent is a cytostatic drug, such as for example, zotaroliums.

In accordance with another embodiment, the coating includes first and second layers adsorbed to the surface of the balloon. The first layer consists of the first therapeutic agent and first excipient and the second layer consists of the second therapeutic agent and the second excipient. In this regard, the first and second layers each have a dissolution rate, the dissolution profile of the first layer being different than the dissolution profile of the second layer.

In accordance with another embodiment, the disclosed subject matter includes a balloon for delivery of a drug. The balloon includes an outer surface having a tunable coating disposed on at least a length of the outer surface, the tunable coating including a cytostatic drug and at least one excipient, the tunable coating having a dissolution rate of about 10 seconds to about 1 hour. Preferably, the dissolution rate consists of 10 seconds to 10 minutes and the excipient is hydrophilic.

In accordance with yet another embodiment, the disclosed subject matter includes a balloon for delivery of a drug. The balloon includes an outer surface having a tunable coating disposed on at least a length of the outer surface, the tunable coating including a cytostatic drug and at least one excipient, wherein the cytostatic drug to excipient weight ratio is from about 20:1 to about 1:20. In accordance with one embodiment, the coating further includes a plasticizer and the excipient to plasticizer weight ratio is from about 20:1 to about 1:20.

In accordance with yet another embodiment, the disclosed subject matter includes a balloon for delivery of a drug. The balloon includes an outer surface having a tunable coating disposed on at least a length of the outer surface, the tunable coating including a cytostatic drug and at least one excipient, wherein the at least one polymeric excipient has a polydispersity index from about 1.05 to about 10, more preferably from 1.05 to 5.

It is to be understood that both the foregoing description is exemplary and is intended to provide further explanation of the disclosed subject matter claimed to a person of ordinary skill in the art. The accompanying drawings are included to illustrate various embodiments of the disclosed subject matter to provide a further understanding of the disclosed subject matter. The exemplified embodiments of the disclosed subject matter are not intended to limit the scope of the claims.

BRIEF DESCRIPTION OF DRAWINGS

The disclosed subject matter will now be described in conjunction with the accompanying drawings in which.

DETAILED DESCRIPTION

Reference will now be made in detail to the various aspects of the disclosed subject matter. The method of the disclosed subject matter will be described in conjunction with the detailed description of the device, the figures and examples provided herein.

The devices and methods presented can be used for delivery within and/or treating of the lumen of a patient. In particular, the disclosed subject matter is particularly suited for treatment of the cardiovascular system of a patient, such as performance of angioplasty and delivery of a balloon expandable medical device, such as a stent, filter and coil.

As disclosed herein, a balloon catheter is provided for delivery of a therapeutic agent, the balloon including an outer surface having a tunable coating disposed on at least a length of the outer surface. The tunable coating includes a therapeutic agent and an excipient. The solubility of the coating in-vivo, the biosolubility, of the coating is tunable based on the substances and concentrations chosen for the therapeutic agent and excipient.

Figure 1A:
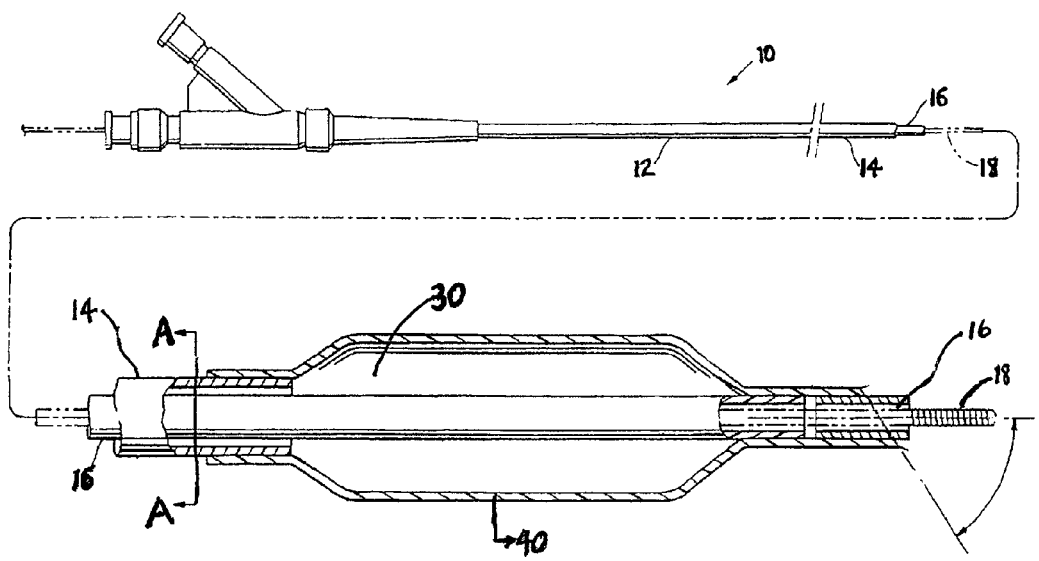
FIG. 1A is a representative embodiment of a planar view of a medical device in accordance with the disclosed subject matter.
Figure 1B:
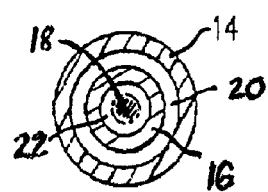
FIG. 1B is a cross-sectional view taken along lines A-A in FIG. 1A in accordance with one embodiment of the disclosed subject matter for illustration and not limitations.

Referring to FIG. 1, for purposes of illustration and not limitation, an exemplary embodiment of balloon catheter device in accordance with the disclosed subject matter is shown schematically in FIGS. 1A and 1B. As depicted in FIGS. 1A and 1B, the balloon catheter device 10 generally includes an elongated catheter shaft 12 having a proximal end and having a distal end and an expandable balloon 30 located proximate to the distal end of the catheter shaft. The expandable balloon has an outer surface and an inner surface disposed at the distal end portion of the catheter shaft. In accordance with the disclosed subject matter, a tunable coating 40 is applied to at least one length of the balloon catheter, the tunable coating including a first therapeutic agent and a first excipient, and a second therapeutic agent and a second excipient, wherein the first and second therapeutic agents have different dissolution rates during balloon inflation. In accordance with a preferred embodiment, as illustrated by way of example and not limitation in FIG. 1A, the coating is applied to at least one length of the outer surface of the balloon catheter.

The elongated catheter shaft 12 comprises an outer tubular member 14 and an inner tubular member 16. The outer tubular member 14 defines an inflation lumen 20 that can be disposed between the proximal end portion and the distal end portion of the catheter shaft 12. Specifically, as illustrated in FIG. 1B, the coaxial relationship between the inner tubular member 16 and the outer tubular member 14 defines an annular inflation lumen 20. The expandable member 30 is placed in fluid communication with the inflation lumen 20. The inflation lumen can supply fluid under pressure, and establish negative pressure to the expandable member. The expandable member 30 can thus be inflated and deflated. The elongated catheter is sized and configured for delivery through a tortuous anatomy, and can further include a guidewire lumen 22 that permits it to be delivered over a guidewire 18. As illustrated in FIG. 1B, the inner tubular member 16 defines the guidewire lumen 22 for the guidewire 18. Although FIGS. 1A and 1B illustrate the guidewire lumen as having an over-the-wire (OTW) construction, the guidewire lumen can be configured as a rapid-exchange (Rx) construction, as is well known in the art.

As disclosed herein, the coating is tunable with respect to its solubility. Therefore, the drug delivery balloon is able to provide the desired delivery kinetics as a result of its tunability. The choice of excipient is key in determining efficacy factors such as, retaining of the therapeutic agent during delivery, releasing of the therapeutic agent during deployment, minimizing systemic dosing, maximizing agent delivery efficiency and therapeutic effect, and preventing particulate generation and related thromboses, among other factors.

As disclosed herein, "tunable" refers to the ability to be tuned or adjusted for desired functioning. Accordingly, a tunable coating refers to a coating that can be adjusted according to various parameter discussed herein.

As disclosed herein, the balloon includes a tunable coating that comprises a therapeutic agent and an excipient. In accordance with one embodiment, the tunable coating includes a first therapeutic agent and a first excipient and can include a second therapeutic agent and a second excipient. The coating has a biosolubility that is tunable based on the substances and concentrations chosen for each of the therapeutic agent and excipient. Preferably, the therapeutic agents have different dissolution rates. The coating can include additional therapeutic agents and excipients.

In accordance with the disclosed subject matter, the solubility of the coating can be adjusted by modifying a number of factors, including excipient type, composition and molecular weight of the excipient, modulation of excipient or polymer properties such as aqueous solubility, octanol/water partition coefficient, HLB (hydrophile-lipophile balance) number, glass transition temperature, degree of amorphous versus crystalline polymer, and orientation. Furthermore, the solubility or dissolution rates of the coating can be adjusted by varying the therapeutic agent concentration, therapeutic agent to excipient ratio, or coating thickness. Accordingly, these factors can be varied in order to provide a coating with the desired solubility and drug delivery kinetics.

The tunable coating provides for dissolution rates during balloon inflation that can be characterized generally as ranging from fast, soluble, intermediate, slow, extra slow, and non-soluble. Depending on the target tissue or vasculature where the therapeutic agent is to be delivered, the coating can be tuned such that the dissolution rate provides for effective drug delivery and uptake. A "fast" coating dissolution rate will typically have a dissolution time of less than 1 minute. A "soluble" coating dissolution rate will typically have a dissolution time ranging from about 1 minute to about 1 hour. An "intermediate" coating dissolution rate will typically have a dissolution time ranging from about 1 hour to about 2 weeks. A "slow" coating dissolution rate will typically have a dissolution time ranging from about 2 weeks to about 3 months. An "extra slow" coating dissolution rate will typically have a dissolution time ranging from about 3 months to 2 years. A "non-soluble" coating dissolution rate will typically have a dissolution time greater than 2 years. However, it shall be noted that the specific dissolution of a coating composition is dependent upon an interplay between input factors and that the dissolution rates provided herein are, therefore, recited as ranges.

The excipients include various oil-based, biosoluble, and biodurable substances that are suitable for the delivery of a therapeutic agent. Biosolubility indicates solubility in a relevant biological media, such as blood. A substance which is not intended to degrade in the body, or which degrades only very slowly, is biodurable. In accordance with a preferred embodiment, the excipients of the disclosed subject matter are water soluble. The excipients can include non-ionic hydrophilic polymers. Non-ionic hydrophilic polymers include, but are not limited to, poly(vinyl pyrrolidone) (PVP, povidone), silk-elastin like polymer, poly(vinyl alcohol), poly(ethylene glycol) (PEG), pluronics (PEO-PPO-PEO), poly(vinyl acetate), poly(ethylene oxide) (PEO), PVP-vinyl acetate (copovidone), PEG-phosphoethanolamine (PEGPE), polysorbate 80 (Tween 80) and polysorbate 20 (Tween 20). Preferably, the molecular weight of non-ionic hydrophilic polymers can be less than 50 kDa for fast solubility. The excipient can also include fatty acids. Further, the excipient can be a lubricious material which improves spreading and uniformity of coating.

In accordance with one embodiment, the excipient consists of a biocompatible plasticizer. Alternatively, the plasticizer can be added to the excipient to keep it soft and pliable. Plasticizers can allow for greater coating flexibility and elongation to prevent coating cracking during inflation or brittleness. Plasticizers include, but are not limited to, glycerol, ethanol, dimethylsulfoxide, ethyl lactate, benzyl alcohol, benzyl benzoate, Cremophor EL, Vitamin E, tocopherol, liquid PEG (MW<1000), triethyl citrate, tributyl citrate, acetyl tributyl citrate, acetyl triethyl citrate, dibutyl phthalate, dibutyl sebacate, dimethyl phthalate, triacetin, propylene glycol, glycerin, 2-pyrridone, and combinations thereof. Preferably, a biocompatible plasticizer is used.

In accordance with yet another embodiment, sugars, polysaccharides or cellulosics, can be used as binders for the particles. Polysaccharides include, but are not limited to, dextran, sulfonated dextran, hydrogenated dextran, chondroitin sulfate, sodium hyaluronate, hyaluronic acid, hyaluronan, chitosan, sodium alginate, sucrose, pectin, mannitol, carboxymethyl cellulose (CMC) sodium, methyl cellulose, ethyl cellulose, hydroxyethyl cellulose, hydroxypropyl cellulose, and hydroxypropylmethylcellulose. Certain negative charged polysaccharides will provide a mucoadhesive effect to enhance tissue drug retention. Furthermore, sugars such as mannitol will provide a decreased hygroscopic effect when blended with more moisture-sensitive active ingredients such as cytostatic drugs or moisture sensitive excipients. Water soluble cellulosic materials can enhance coating strength or brittleness.

In accordance with yet another embodiment, anti-coagulants can be used as an excipient. For example, heparin based polysaccharides can provide a minimally thrombogenic surface to prevent blood clotting on the balloon surface or minimize platelet activation induced by the procedure. Heparin based polysaccharides include, but are not limited to, heparin, heparin sulfate, heparin disaccharides, heparin fraction 1, heparin fraction 2, low molecular weight heparin, heparin ammonium, heparin calcium, heparin lithium, heparin lithium, and heparin zinc lithium. Low molecular weight heparin includes centaxarin, periodate-oxidized heparin, heparin sodium end-amidated, heparin sodium, and nitrous acid delaminated.

In accordance with a preferred embodiment of the disclosed subject matter, the excipient possesses a mucoadhesive property. This mucoadhesive property of the binder will lead to longer drug retention within the coating adhered to the vessel wall. In particular, positively charged excipients such as chitosan, negatively charged excipients such as some polysaccharides (e.g. carboxymethylcellulose, sodium hyaluronate, sodium alginate) and some non-ionic hydrophilic polymers exhibit mucoadhesive properties. Any above carboxylated materials can also be lightly activated with esters such as nitrophenolate or NHS-esters (N-hydroxy succinimide) for increased mucoadhesiveness. Alternatively, any above materials can be lightly thiolated for increased mucoadhesiveness and continued solubility.

Additionally or alternatively, the excipient is or includes a contrast agent, including but not limited to, Iopromide (Ultravist), Ioxaglate (Hexabrix), Ioversol (Optiray), Iopamidol (Isovue), Diatrixoate (Conray), Iodixanol (Visipaque), Iohexyl (Omnipaque), and Iotrolan. At an intermediate coating thickness, a lower molecular weight (<1 kDa) hydrophilic contrast agent such as Iopromide (Ultravist) would enable faster therapeutic release and a slightly higher viscous coating of the vessel wall as compared with drug alone. The contrast agents are lipophilic and can aid in drug uptake and retention into the tissue wall. In accordance with one embodiment, Ultravist and Optiray can be used given their more benign history of effects to smooth muscle and endothelial cells.

In accordance with yet another embodiment, excipients can consist of carboxylated aromatics similar in molecular structure to the structure used in contrast agents but without iodide substituents. These negatively charged carboxylated aromatic structures can be alkylated (C2-C12) to optimize drug tissue uptake, or halogenated with fluoride, chloride or bromide for the same reason. The negatively charged structures are beneficial for tissue adhesiveness.

Table 1 provides non-limiting examples of the solubility data for excipients that can be used in accordance with the disclosed subject matter:

TABLE 1

Solubility Enhancement of a Therapeutic Agent with Select Excipients

| Solution (5% w/w) | Zotarolimus Solubility (ug/ml, n = 3) |
| --- | --- |
| Phosphate buffered saline | 0.53 |
| PVP C-17 | 5.6 ± 1.6 |
| Hydroxypropyl-β-cyclodextrin | 11.6 ± 3.1 |

TABLE 1-continued

Solubility Enhancement of a Therapeutic Agent with Select Excipients

| Solution (5% w/w) | Zotarolimus Solubility (ug/ml, n = 3) |
| --- | --- |
| PEG 400 | 31.5 ± 3.5 |
| Glycerol | 43.2 ± 30.1 |
| 5% γ-Cyclodextrin | 55.3 ± 34.3 |
| Vitamin E TPGS | 512 ± 49.5 |
| Tween 20 | 732 ± 94.7 |
| 18:0 PEG2000 PE (PEG-PE)* | 1020 ± 417 |

*1,2-distearoyl-sn-glycero-3-phosphoethanolamine-N-[methoxy(polyethyleneglycol)-2000] (ammonium salt)

As illustrated, in Table 1 the excipients provide for increased solubility for the cytostatic drug, zotarolimus, as compared to saline alone. The excipients Vitamin E TPGS, Tween 20 and PEG-PE demonstrate the largest increase in zotarolimus solubility.

Table 2 provides non-limiting examples of coating dissolution rates during balloon inflation and representative excipient examples.

TABLE 2

Examples of Delivery Kinetics and Expected Variable Ranges for Balloon Coatings

| Coating Dissolution Rate (during balloon inflation) | Coating Dissolution Time | Representative Excipient Example |
| --- | --- | --- |
| Fast | <1 minute | Poly(vinylpyrrolidone) (PVP) (MW <60 kDa) or Polyethylene glycol (PEG) (lower MW <35 kDa) |
| Soluble | 1 min to 1 hour | Poly(vinylpyrrolidone) (PVP) (MW >60 kDa) or Polyethylene oxide (PEO) (higher MW >100 kDa) |
| Intermediate | 1 hour to 2 weeks | Silk-elastin like protein polymers |
| Slow | 2 weeks-3 months | Biodegradable polymer such as Poly(D,L-lactide-co-glycolide) (PLGA) (50:50) |
| Extra Slow | 3 months-2 years | Biodegradable polymer such as Poly(L-lactide-co-ε-caprolactone) (PLLA:PCL) (70:30) |
| Non-Soluble | >2 years | Durable polymer such as Poly(vinylidene fluoride-co-hexafluoropropylene) |

As illustrated in Table 2 above, for a "fast" coating dissolution rate, representative excipient examples include, without limitation, polyvinylpyrrolidone (PVP) with a molecular weight less than about 60 kDalton, or polyethylene glycol (PEG) having a molecular weight less than about 35 kDa. The drug delivery mechanism and kinetics expected with this representative example include the release of the therapeutic agent with the coating during inflation. Further, the potential mucoadhesive polymer increases drug retention time on tissue or vasculature. Alternatively, or additionally, the lipophilic additive increases drug uptake in tissue.

As illustrated in Table 2 above, for a "soluble" coating dissolution rate, representative excipient examples include, without limitation, polyvinylpyrrolidone (PVP) having a molecular weight greater than about 60 kDa, or polyethylene glycol (PEG) having a molecular weight greater than about 100 kDa. The drug delivery mechanism and kinetics expected with this representative example are similar to that of the "fast" coating dissolution rate, however, the slightly slower dissolution time allows for less drug wash off during balloon delivery before inflation.

As illustrated in Table 2 above, for an "intermediate" coating dissolution rate, representative excipient examples include, without limitation, silk-elastin like protein polymers. The drug delivery mechanism and kinetics expected with this representative example provides for enhanced systemic drug loss protection and absence of short-term solubility, therefore allowing for enhanced particulate safety. For an "intermediate" dissolution rate, the therapeutic agent is not released together with the coating but from the coating. The therapeutic agent release kinetics and transfer to tissue are significantly enhanced by mechanical action during balloon inflation. Typically, these type of coating materials can by hydrophilic and can swell to some extent upon hydration to aid in fast drug release.

As illustrated in Table 2 above, for a "slow" coating dissolution rate, representative excipient examples include, without limitation, biodegradable polymers such as Poly(D,L-lactide-co-glycolide) (PLGA) (50:50). The coatings from biodegradable hydrophobic polymers will offer enhanced systemic drug loss protection and a better particulate safety profile. The therapeutic agent is not released together with the coating but from the coating. Drug release kinetics and transfer to tissue are significantly enhanced by mechanical action during balloon inflation. Techniques such as using a thin coating, a polymer with a low glass transition temperature (Tg), and amorphous material or low crystalline material can provide for a more rapid drug release profile when using a biodegradable polymer.

As illustrated in Table 2 above, for an "extra slow" coating dissolution rate, representative excipient examples include, without limitation, biodegradable polymers such as poly(L-lactide-co-$\epsilon$-caprolactone) (PLLA:PCL) (70:30). The drug delivery mechanism and kinetics are similar to a "slow" coating dissolution rate, however the degradation time is significantly extended. These coatings will have more long term degradation and mechanical stability under storage.

As illustrated above, for a "non-soluble" coating dissolution rate, representative excipient examples include, without limitation, durable polymers such as poly(vinylidene fluoride-co-hexafluoropropylene). The drug delivery mechanism and kinetics are similar to both a "slow" and "extra slow" coating dissolution rate, however the material is non-biodegradable. These non-soluble coatings will have the most chemical and mechanical stability under storage than other types.

In accordance with the disclosed subject matter, the outer surface of the balloon has a tunable coating that is disposed on at least a length of the outer surface. Preferably, the tunable coating includes a first therapeutic agent and a first excipient and a second therapeutic agent and a second excipient. In accordance with a preferred embodiment, the first and second therapeutic agents have different dissolution rates during balloon inflation. Thus, the desired coating dissolution rates can be tunable and achieved as desired for either drug kinetics or safety profile. The delivery of the therapeutic agents can be modified and optimized to meet the therapeutic need. Furthermore, depending on the excipients used, the therapeutic agents can be released from the excipient or coating or with the excipient or coating. In accordance with one embodiment, the first therapeutic agent is released from the coating, and the second therapeutic agent is released with the coating.

In one embodiment, the first therapeutic agent is different than the second therapeutic agent. Alternatively, however, the therapeutic agents can be the same.

In accordance with another embodiment, the coating can also include a third therapeutic agent and a third excipient. The therapeutic agents and excipients can be applied simultaneously to the balloon surface or they can be applied separately.

In accordance with yet another embodiment, the disclosed subject matter includes a balloon having a the tunable coating including a cytostatic drug and at least one excipient, wherein the coating includes at least one polymeric component having a polydispersity index from about 1.05 to about 10, more preferably from 1.05 to 5. The polydispersity index (PDI), is a measure of the distribution of molecular mass in a given polymer sample. The PDI calculated is the weight average molecular weight divided by the number average molecular weight. It indicates the distribution of individual molecular masses in a batch of polymers. A smaller PDI value should provide a more consistent dissolution rate among the polymeric excipient molecules.

In accordance with the disclosed subject matter, the coating can be applied to the medical device by processes such as dip-coating, pipette coating, syringe coating, air assisted spraying, electrostatic spraying, piezoelectric spraying, spray drying, pneumatic spray, ultrasonic spray, spray with patterning, electrospinning, direct fluid application, or other means as known to those skilled in the art. The coating can be applied over at least a length or the entirety of the balloon or medical device. By way of example, and not limitation, certain coating processes that can be used with the instant disclosed subject matter are described in U.S. Pat. No. 6,669,980 to Hansen; U.S. Pat. No. 7,241,344 to Worsham; and U.S. Publication No. 20040234748 to Stenzel, the entire disclosures of which are hereby incorporated by reference. In accordance with one embodiment of the disclosed subject matter, the medical device is a balloon catheter and the coating can be applied to either a folded or inflated balloon. Furthermore, the coating can be directly applied into the folds of the folded balloons. The coating characteristics are affected by process variables. For example, for dip-coating process, coating quality and thickness can vary as an effect of variables such as number, rate, and depth of dips along with drying time and temperature.

In accordance with one embodiment, the balloon can be sprayed with therapeutic agent encapsulated in the durable excipient solution. Spray solvents can consist of the following class III solvents including but not limited to acetone, anisole, 1-butanol, 2-butanol, butyl acetate, tert-butylmethyl ether, cumene, dimethyl sulfoxide, ethanol, ethyl acetate, ethyl ether, ethyl formate, heptane, hexane, cyclohexane, isobutyl acetate, isopropyl acetate, methyl acetate, 3-methyl-1-butanol, methylethyl ketone, methylisobutyl ketone, cyclohexanone, 2-methyl-1-propanol, pentanel, 1-pentanol, 1-propanol, and propyl acetate, or blends thereof.

Additional spray solvents that can be used or blended with class III solvents include class II spray solvents. The class II spray solvents include but are not limited to, acetonitrile, chloroform, 1,2-dichloroethane, dichloromethane, 1,2-dimethyloxyethene, N,N-dimethylacetamide, N,N-dimethylformamide, 1,4-dioxane, 2-ethoxyethanol, ethylene glycol, formamide, hexane, methanol, 2-methoxyethanol, methyl butyl ketone, methylcyclohexane, N-methylpyrrolidone, nitromethane, pyridine, sulfolane, tetrahydrofuran, tetralin, toluene, 1,1,2-trichloroethene, and xylene.

In accordance with the disclosed subject matter, the excipient and therapeutic agent coating process can occur aseptically or be followed with terminal sterilization method such as E-beam, gamma irradiation, or ethylene oxide sterilization.

In accordance with the disclosed subject matter, excipients are utilized together with the therapeutic agent in the coating at ratios ranging from 1:20 to 20:1 excipient:drug by weight, preferably from 1:10 to 10:1, more preferably from 1:2 to 2:1. Preferably, the coating includes a plasticizer. In this regards, the excipient to plasticizer weight ratio is from about 20:1 to about 1:20, more preferably from 10:1 to 1:1.

In accordance with another embodiment of the disclosed subject matter, the coating includes various layers. In one embodiment, the coating includes first and second layers adsorbed to the surface of the balloon. The first layer typically consists of one therapeutic agent and one excipient and the second layer typically consists of a second therapeutic agent and second excipient. The drug coated balloon is designed such that the first and second layers each have a dissolution rate. Preferably, the dissolution profile of the first layer is different than the dissolution profile of the second layer. Providing layers with various dissolution profiles allows the coating to be tuned to an optimized range.

In accordance with yet another embodiment, the disclosed subject matter includes a method of increasing the efficiency of therapeutic transfer to a body lumen by implanting or inserting a medical device in a body lumen. The medical device includes an expandable member having an outer surface and a coating disposed on the outer surface of the medical device, the coating including a therapeutic agent and an excipient.

For example and not limitation, the at least one therapeutic agent can include anti-proliferative, anti-inflammatory, antineoplastic, antiplatelet, anti-coagulant, anti-fibrin, antithrombotic, antimitotic, antibiotic, antiallergic and antioxidant compounds. Thus, the therapeutic agent can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, and a retroviral vector. Preferably, however, the therapeutic agents include a cytostatic drug. The term "cytostatic" as used herein means a drug that mitigates cell proliferation, allows cell migration, and does not induce cell toxicity. These cytostatic drugs, include for the purpose of illustration and without limitation, macrolide antibiotics, rapamycin, everolimus, zotarolimus, biolimus, novolimus, myolimus, temsirolimus, deforolimus, structural derivatives and functional analogues of rapamycin, structural derivatives and functional analogues of everolimus, structural derivatives and functional analogues of zotarolimus and any macrolide immunosuppressive drugs. The term "antiproliferative" as used herein means a drug used to inhibit cell growth, such as chemotherapeutic drugs. Some non-limiting examples of antiproliferative drugs include taxanes, paclitaxel, and protaxel.

Therefore, in accordance with a preferred embodiment, a balloon for delivery of a cytostatic drug is provided. The outer surface of the balloon includes a tunable coating, the tunable coating including a first cytostatic drug and a first excipient and a second cytostatic drug and a second excipient. The first and second cytostatic drugs preferably have different dissolution rates during balloon inflation. The various dissolution rates allow for more effective and efficient delivery of the therapeutic agent.

With reference to the balloon construction, a polymeric expandable balloon material is preferred. For example, the polymeric material utilized to form the balloon body can be compliant, non-compliant or semi-compliant polymeric material or polymeric blends.

In one embodiment, the polymeric material is compliant such as but not limited to a polyamide/polyether block copolymer (commonly referred to as PEBA or polyether-block-amide). Preferably, the polyamide and polyether segments of the block copolymers can be linked through amide or ester linkages. The polyamide block can be selected from various aliphatic or aromatic polyamides known in the art. Preferably, the polyamide is aliphatic. Some non-limiting examples include nylon 12, nylon 11, nylon 9, nylon 6, nylon 6/12, nylon 6/11, nylon 6/9, and nylon 6/6. Preferably, the polyamide is nylon 12. The polyether block can be selected from various polyethers known in the art. Some non-limiting examples of polyether segments include poly(tetramethylene ether), tetramethylene ether, polyethylene glycol, polypropylene glycol, poly(pentamethylene ether) and poly(hexamethylene ether). Commercially available PEBA material can also be utilized such as for example, PEBAX® materials supplied by Arkema (France). Various techniques for forming a balloon from polyamide/polyether block copolymer is known in the art. One such example is disclosed in U.S. Pat. No. 6,406,457 to Wang, the disclosure of which is incorporated by reference.

In another embodiment, the balloon material is formed from polyamides. Preferably, the polyamide has substantial tensile strength, be resistant to pin-holing even after folding and unfolding, and be generally scratch resistant, such as those disclosed in U.S. Pat. No. 6,500,148 to Pinchuk, the disclosure of which is incorporated herein by reference. Some non-limiting examples of polyamide materials suitable for the balloon include nylon 12, nylon 11, nylon 9, nylon 69 and nylon 66. Preferably, the polyamide is nylon 12. Other suitable materials for constructing non-compliant balloons are polyesters such as poly(ethylene terephthalate) (PET), Hytrel thermoplastic polyester and polyethylene.

In another embodiment, the balloon is formed of a polyurethane material, such as TECOTHANE® (Thermedics). TECOTHANE® is a thermoplastic, aromatic, polyether polyurethane synthesized from methylene disocyanate (MDI), polytetramethylene ether glycol (PTMEG) and 1,4 butanediol chain extender. TECOTHANE® grade 1065D is presently preferred, and has a Shore durometer of 65D, an elongation at break of about 300%, and a high tensile strength at yield of about 10,000 psi. However, other suitable grades can be used, including TECOTHANE® 1075D, having a Shore D hardness of 75. Other suitable compliant polymeric materials include ENGAGE® (DuPont Dow Elastomers (an ethylene alpha-olefin polymer) and EXACT® (Exxon Chemical), both of which are thermoplastic polymers. Other suitable compliant materials include, but are not limited to, elastomeric silicones, latexes, and urethanes.

The compliant material can be cross linked or uncrosslinked, depending upon the balloon material and characteristics required for a particular application. The presently preferred polyurethane balloon materials are not crosslinked. However, other suitable materials, such as the polyolefinic polymers ENGAGE® and EXACT®, are preferably crosslinked. By crosslinking the balloon compliant material, the final inflated balloon size can be controlled. Conventional crosslinking techniques can be used including thermal treatment and E-beam exposure. After crosslinking, initial pressurization, expansion, and preshrinking, the balloon will thereafter expand in a controlled manner to a reproducible diameter in response to a given inflation pressure, and thereby avoid overexpanding the stent (if used in a stent delivery system) to an undesirably large diameter.

In one embodiment, the balloon is formed from a low tensile set polymer such as a silicone-polyurethane copolymer. Preferably, the silicone-polyurethane is an ether urethane and more specifically an aliphatic ether urethane such as PURSIL AL 575A and PURSIL AL10, (Polymer Technology Group), and ELAST-EON 3-70A, (Elastomedics), which are silicone polyether urethane copolymers, and more specifically, aliphatic ether urethane cosiloxanes. In an alternative embodiment, the low tensile set polymer is a diene polymer. A variety of suitable diene polymers can be used such as, but not limited to, an isoprene such as an AB and ABA poly(styrene-block-isoprene), a neoprene, an AB and ABA poly(styrene-block-butadiene) such as styrene butadiene styrene (SBS) and styrene butadiene rubber (SBR), and 1,4-polybutadiene. Preferably, the diene polymer is an isoprene including isoprene copolymers and isoprene block copolymers such as poly(styrene-block-isoprene). A presently preferred isoprene is a styrene-isoprene-styrene block copolymer, such as Kraton 1161K available from Kraton, Inc. However, a variety of suitable isoprenes can be used including HT 200 available from Apex Medical, Kraton R 310 available from Kraton, and isoprene (i.e., 2-methyl-1,3-butadiene) available from Dupont Elastomers. Neoprene grades useful in the disclosed subject matter include HT 501 available from Apex Medical, and neoprene (i.e., polychloroprene) available from Dupont Elastomers, including Neoprene G, W, T and A types available from Dupont Elastomers.

In accordance with another aspect of the disclosed subject matter, the outer surface of the balloon is modified. In this regard, the balloon surface can include a textured surface, roughened surface, voids, spines, channels, dimples, pores, or microcapsules or a combination thereof, as will be described below.

In accordance with in the disclosed subject matter, the balloon does not include a stent or is free of a stent. However, a stent can be mounted onto the coated balloon. The stent will not detrimentally affect coating integrity or drug delivery. The type of stent that can be used includes, but is not limited to, bare metal stent, balloon expandable stent, self expanding stent, drug eluting stent, prohealing stent, and self-expanding vulnerable plaque implant. The balloon can be coated independently of the stent or in conjunction with the stent coating process. The stent coating can contain the same or different therapeutic agents from the balloon catheter or expandable member. However, the particular coating on the balloon catheter or expandable member preferably has distinct release kinetics from the therapeutic coating on the stent.

In one embodiment of the disclosed subject matter, the balloon is formed of a porous elastomeric material having at least one void formed in the wall of the balloon surface. For example, the entire cross section of the balloon can contain a plurality of voids. Alternatively, the plurality of void can be distributed along select lengths of the balloon outer surface. For example and not limitation, the plurality of voids can be distributed only along only the working section of the balloon. The voids define an open space within the outer surface of the balloon. Preferably, the therapeutic agent is dispersed within the space defined by the plurality of voids across the cross section of the balloon outer surface.

In operation, the therapeutic agent is released or is expelled from the pores upon inflation of the balloon. In this regard, the durometer of the polymeric material of the balloon surface and in particular the depression of the void is sufficiently flexible to allow for expulsion of the therapeutic agent and/or coating contained within the plurality of voids upon inflation of the balloon. The expelled coating with therapeutic agent is released into the vessel lumen or into the tissue surrounding and contacting the inflated balloon.

In another embodiment, the balloon includes protrusions configured to contact or penetrate the arterial wall of a vessel upon inflation of the balloon. A coating containing therapeutic agent is disposed on the protrusions and when inflated the coating and/or therapeutic agent coats the tissue of the arterial wall. Alternatively, the balloon can include two concentric balloons in a nesting configuration. The coating with therapeutic agent is disposed between the two concentric balloons. Thus, the space between the two concentric balloons; one being an interior balloon and the other being an exterior balloon, acts as a reservoir. In this regard, the protrusions can include apertures for expulsion of the coating and/or therapeutic agent upon inflation of the interior and exterior concentric balloons. For example, as described in U.S. Pat. No. 6,991,617 to Hektner, the disclosure of which is incorporated herein by reference thereto. In another embodiment, the balloon can include longitudinal protrusions configured to form ridges on the balloon surface. As described in U.S. Pat. No. 7,273,417 to Wang, the entire disclosure of which is incorporated herein by reference, the ridges can be formed of filaments spaced equidistantly apart around the circumference of the balloon. However, a larger or smaller number of ridges can alternatively be used. The longitudinal ridges can be fully or partially enveloped by the polymeric material of the balloon.

In yet another embodiment of the disclosed subject matter, the balloon can include microcapsules on its outer surface. In this regard, the microcapsules are configured to encompass the coating and/or therapeutic agent. Upon inflation of the balloon the microcapsules located on the surface of the balloon contact the tissue of the arterial wall. Alternatively, the microcapsules can be formed in the wall of the balloon surface. The coating and/or therapeutic agent can be released from the microcapsules by fracturing of the microcapsules and/or diffusion from the microcapsule into the arterial wall. The microcapsules can be fabricated in accordance with the methods disclosed in U.S. Pat. No. 5,1023,402 to Dror or U.S. Pat. No. 6,129,705 to Grantz and the patents referenced therein, each of which is incorporated herein by reference in its entirety.

In accordance with another aspect of the disclosed subject matter, if desired, a protective sheath can be utilized to protect the coating from being rubbed off of the balloon during the movement of the coated balloon through the body lumen. The sheath is preferably made from an elastic and resilient material which conforms to the shape of the balloon and in particular is capable of expanding upon inflation of the balloon. The sheath preferably includes apertures along a length thereof. In operation, the inflation of the balloon causes the apertures of the sheath to widen for release of the coating and/or therapeutic agent to the tissue of the arterial wall. Preferably, the sheath has a thickness less than 10 mils. However, other thicknesses are possible.

In another embodiment, the sheath has at least one longitudinal line of weakness allowing the sheath to rupture upon inflation of the balloon and the release of the coating and/or therapeutic agent onto the tissue of the arterial wall of the vessel. Preferably, the sheath is formed from polymeric material known to be suitable for use in balloon catheters. Preferably, the sheath material is an elastomeric material which will also spring back when it splits to expose more of the body lumen to the coating. The line of weakness could be provided by various techniques known in the art. However, one non-limiting examples include perforating the sheath material. In operation, the sheath is placed over the coated balloon while in the deflated state. When the coated balloon is inflated, the sheath is expanded to the extent that it exceeds its elastic limit at the line of weakness and bursts to expose and therefore release the coating and/or therapeutic agent to the tissue of the arterial wall or vessel lumen. For example, see U.S. Pat. No. 5,370,614 to Amundson, the entire disclosure of which is incorporated by reference.

In accordance with an another embodiment, an outer fibrous coating can be electrospun or stretched onto the medical device or balloon catheter to prevent drug loss during delivery. During balloon inflation, the coating is stretched and allows for coating dissolution and release. The fiber diameters and material properties can be fine tuned for optimal pore size and to release the particles containing the therapeutic agent. Fibrous coatings on expandable members are described in U.S. patent application Ser. No. 12/237,998 to R. von Oepen and U.S. patent application Ser. No. 12/238,026 to K. Ehrenreich, the disclosures of which are incorporated by reference in their entirety.

It is to be noted that the term "a" entity or "an" entity refers to one or more of that entity. For example, a protein refers to one or more proteins or at least one protein. As such, the teens "a", "an", "one or more", and "at least one" can be used interchangeably herein. The terms "comprising," "including," and "having" can also be used interchangeably. In addition, the terms "amount" and "level" are also interchangeable and can be used to describe a concentration or a specific quantity. Furthermore, the term "selected from the group consisting of" refers to one or more members of the group in the list that follows, including mixtures (i.e. combinations) of two or more members.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to +/−20%, preferably up to +/−10%, more preferably up to +/−5%, and more preferably still up to +/−1% of a given value. Alternatively, particularly with respect to biological systems or processes, the term can mean within an order of magnitude, preferably within 5-fold, and more preferably within 2-fold, of a value. With reference to pharmaceutical compositions, the term "about" refers to a range that is acceptable for quality control standards of a product approved by regulatory authorities.

EXAMPLES

The present application is further described by means of the examples, presented below. The use of such examples is illustrative only and in no way limits the scope and meaning of the disclosed subject matter or of any exemplified term.

Example A

To simulate drug release from a drug coated balloon, a three step in vitro release method was developed. This method consists of a sequential dip release in 37° C. porcine serum for 1 min, inflation release in 37° C. porcine serum for 1 min and extraction release in 50% acetonitrile solution designed to mimic the balloon release during delivery to the lesion, drug delivery on inflation and the remaining drug on the balloon respectively. The resulting zotarolimus concentrations in the supernatant are measured by liquid chromatography mass spectrometry (LCMS) and drug from the extraction measured by high performance liquid chromatography (HPLC).

Figure 2:
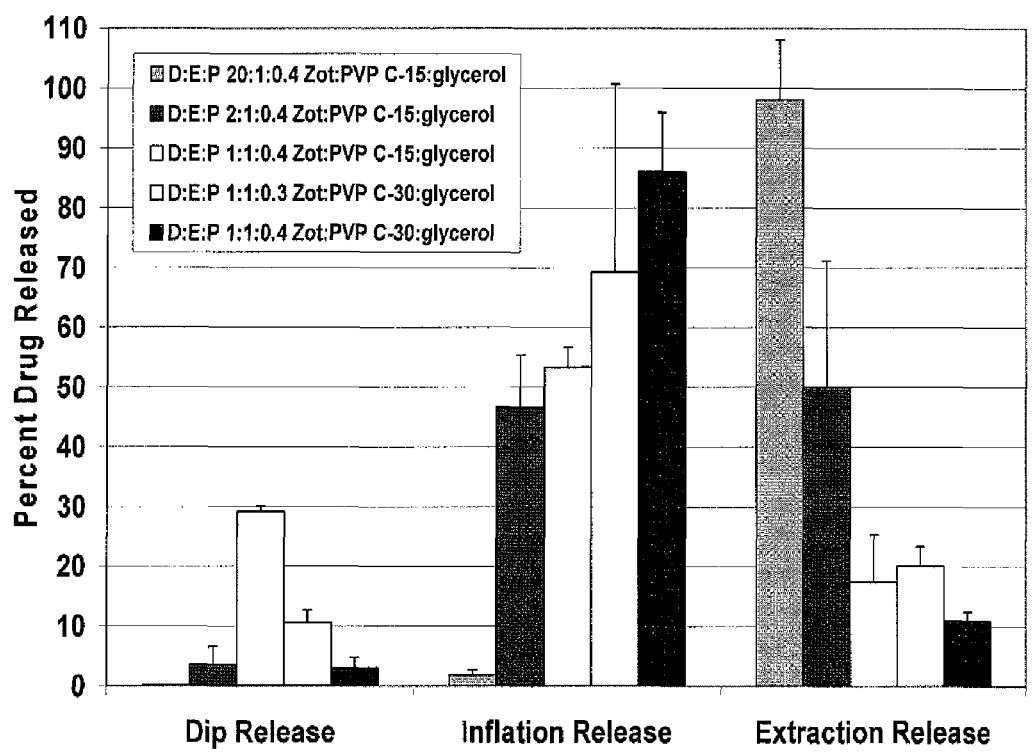
FIG. 2 is a graph illustrating percent drug release as a function of drug, excipient and plasticizer ratio (D:E:P) and poly(vinylpyrrolidone) K value in accordance with one embodiment of the disclosed subject matter.

This in vitro release method was used to evaluate the drug release from zotarolimus (Zot):polyvinylpyrrolidone (PVP): glycerol drug coated balloons as a function of drug:excipient: plasticizer ratio (D:E:P) and PVP K-value. For the combined dip release and inflation release that simulates coating dissolution rate and drug delivery from a drug coated balloon, it is shown in FIG. 2 that a higher drug to excipient ratio such as D:E:P 20:1:0.4 resulted in a "soluble" coating dissolution rate with a dissolution time in the range of 1 min to 1 h releasing less than 5% of drug in 2 min. For lower D:E:P ratios and increasing amounts of plasticizer, the Zot:PVP:glycerol formulation demonstated a "fast" dissolution rate, that is, less than 1 min releasing up to 90% of drug in 2 min. For a lower molecular weight or PVP K-value such as PVP C-15, the coating dissolution rate and drug release during the dip release was further increased to 30%, as compared to the PVP C-30 coating at the same 1:1:0.4 D:E:P ratio which demonstrated less than 5% dip release. The K-Values of C-15 and C-30 designate PVP K value for low endotoxin grade.

Example B

To provide an intermediate coating dissolution time, silk-elastin like protein polymers can be used to formulate the cytostatic drug and coat the balloon from an organic aqueous blend solvent. For example everolimus can be formulated with a physically cross-linked silk-elastin like protein polymer at a 1:1 D:E ratio. As demonstrated in FIG. 3, for 1:1 everolimus:silk-elastin, an intermediate coating dissolution and drug release can be obtained with approximately one-third of everolimus dissolved on delivery, an additional one-third delivered on expansion and the remaining one-third of everolimus remaining on the balloon within the hydrated coating. The physically cross-linked silk-elastin like protein polymer would swell on delivery over a few minutes of hydration but ultimately dissolves over weeks for an intermediate coating dissolution time.

Example C

Figure 3:
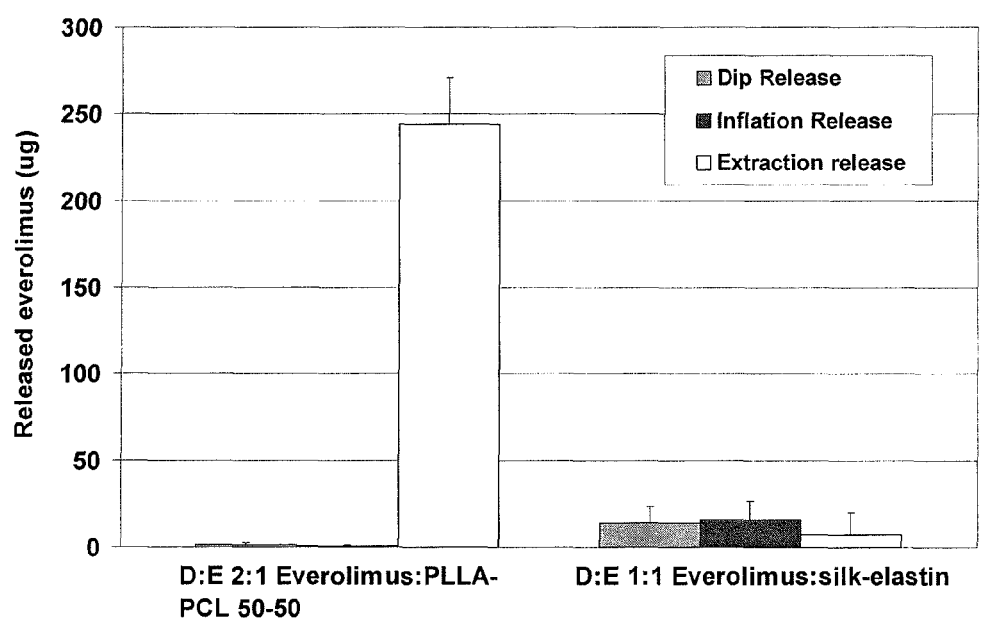
FIG. 3 is a graph illustrating the amount of released everoliums as a function of release type and excipient in accordance with one embodiment of the disclosed subject matter.

To provide for a slow coating dissolution time and reduced drug loss on delivery, a bioabsorbable elastomeric polymer such as poly(L-lactide-co-glycolide) (PLLA-PCL) 50-50 can be formulated together with everolimus at a 2:1 D:E ratio from organic solvent. As shown in FIG. 3, less than 2 ug or 1% of the everolimus loading is released upon dip release for the PLLA-PCL formulation. This slow dissolution coating would be expected to ultimately bioabsorb over months.

The disclosed subject matter can be embodied in other specific forms without departing from its spirit or essential characteristics. The described embodiments are to be considered in all respects only as illustrative and not restrictive. Thus, it is intended that the disclosed subject matter include modifications and variations that are within the scope of the appended claims and their equivalents. All references recited herein are incorporated herein in their entirety by specific reference.

What is claimed is:

1. A balloon for delivery of a drug, the balloon comprising a body having an outer surface; and
a coating disposed on at least a length of the outer surface, the coating including zotarolimus and at least one excipient, wherein the zotarolimus to excipient weight ratio is from about 20:1 to about 1:20, wherein the at least one excipient includes polyvinylpyrrolidone, and further wherein the at least one excipient increases the solubility of the zotarolimus to between 4 µg/ml to 1437 µg/ml.

2. The balloon of claim 1, wherein the zotarolimus to excipient weight ratio is from about 2:1 to about 1:2.

3. The balloon of claim 1, wherein the coating further includes a plasticizer.

4. The balloon of claim 3, wherein the excipient to plasticizer weight ratio is from about 20:1 to about 1:20.

5. The balloon of claim 4, wherein the excipient to plasticizer weight ratio is from about 10:1 to about 1:1.

6. The balloon of claim 3, wherein the plasticizer is glycerol.

7. The balloon of claim 1, wherein the at least one excipient includes a blend of polyvinylpyrrolidone having two different average molecular weights.

8. The balloon of claim 1, wherein the at least one excipient is blended with a contrast agent.

9. The balloon of claim 1, wherein the at least one excipient includes a polymer having a molecular weight of less than about 35 kDalton.

10. The balloon of claim 1, further comprising a second excipient, wherein the second excipient is a polymer having a molecular weight greater than about 100 kDalton.

* * * * *